(12) United States Patent
Halada et al.

(10) Patent No.: US 9,518,077 B2
(45) Date of Patent: Dec. 13, 2016

(54) ELECTROCHEMICAL SYNTHESIS OF CHLORO-CHITOSAN

(71) Applicant: The Research Foundation for the State University of New York, Albany, NY (US)

(72) Inventors: Gary P. Halada, Baiting Hollow, NY (US); Prashant Kumar Jha, Palatine, IL (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 14/374,948

(22) PCT Filed: Feb. 1, 2013

(86) PCT No.: PCT/US2013/024307
§ 371 (c)(1),
(2) Date: Jul. 28, 2014

(87) PCT Pub. No.: WO2013/116619
PCT Pub. Date: Aug. 8, 2013

(65) Prior Publication Data
US 2015/0011742 A1    Jan. 8, 2015

Related U.S. Application Data

(60) Provisional application No. 61/594,619, filed on Feb. 3, 2012.

(51) Int. Cl.
| | | |
|---|---|---|
| *C08B 37/08* | (2006.01) | |
| *C07H 5/00* | (2006.01) | |
| *C08L 5/08* | (2006.01) | |
| *C08J 3/075* | (2006.01) | |
| *C05C 11/00* | (2006.01) | |
| *C25B 3/02* | (2006.01) | |
| *A61L 27/20* | (2006.01) | |
| *A61L 27/54* | (2006.01) | |
| *A61K 47/36* | (2006.01) | |

(52) U.S. Cl.
CPC ............... *C07H 5/00* (2013.01); *A61L 27/20* (2013.01); *A61L 27/54* (2013.01); *C05C 11/00* (2013.01); *C08B 37/003* (2013.01); *C08J 3/075* (2013.01); *C08L 5/08* (2013.01); *C25B 3/02* (2013.01); *A61K 47/36* (2013.01); *A61L 2300/404* (2013.01); *C08J 2305/08* (2013.01)

(58) Field of Classification Search
CPC .......... C07H 5/02; C07H 1/00; C08B 37/003; C08L 5/08; C08J 3/07; C25B 3/02

USPC ............................................. 536/20; 205/421
See application file for complete search history.

(56) References Cited

U.S. PATENT DOCUMENTS

| | | | |
|---|---|---|---|
| 2,967,807 A * | 1/1961 | Miller | ........................ C25B 1/36 204/266 |
| 5,204,452 A | 4/1993 | Dingilian et al. | |
| 5,336,415 A | 8/1994 | Deans | |
| 5,362,717 A * | 11/1994 | Dingilian | .............. C08B 37/003 514/55 |
| 5,996,278 A | 12/1999 | Takaya et al. | |
| 6,409,895 B1 * | 6/2002 | Ponzano | ................... C25B 9/16 204/260 |
| 2005/0079198 A1 | 4/2005 | Nies et al. | |
| 2007/0128286 A1 | 6/2007 | Twu et al. | |
| 2007/0172821 A1 | 7/2007 | Wu et al. | |
| 2009/0252803 A1 | 10/2009 | Yuan et al. | |
| 2009/0258041 A1 | 10/2009 | Mongiat et al. | |
| 2010/0223716 A1 | 9/2010 | Howard, Jr. | |

FOREIGN PATENT DOCUMENTS

WO    2011106526 A2    9/2011

OTHER PUBLICATIONS

Nucleophilic Substitution Reactions. McGraw-Hill Higher Education. Published Mar. 27, 2007 at: <http://www.mhhe.com/physsci/chemistry/carey/student/olc/graphics/carey04oc/ref/ch04nucle.htttml#1>. Archived on Nov. 23, 2001 at <http://web.archive.org/web/20011123004137/http://www.mhhe.com/physsci/chemistry/carey/student/olc/graphics/carey04oc/ref/ch04nucle.html>.
First Office Action issued in China in Appl. No. CN 201380007967.6 dated Oct. 10, 2015.
Zhang, et al., "pH- and Voltage-Responsive Chitosan Hydrogel through Covalent Cross-Linking with Catechol", The Journal of Physical Chemistry B, vol. 116, pp. 1579-1585 (2012).
Extended European Search Report from Appl. No. 13743671.3 dated Sep. 25, 2015.

* cited by examiner

*Primary Examiner* — Scarlett Goon
(74) *Attorney, Agent, or Firm* — Carter, DeLuca, Farrell & Schmidt, LLP

(57) ABSTRACT

The present disclosure provides methods for producing chitosan derivatives and the derivatives formed by these methods. The processes of the present disclosure utilize electrochemical methods to functionalize and/or modify amine and/or hydroxyl groups present on chitosan, to form new derivatives. In embodiments, a chloro-chitosan derivative may be prepared. The altered cationic affinity of these derivatives make them excellent candidates for biomedical applications, including pharmaceuticals, as well as food applications.

5 Claims, 2 Drawing Sheets

ELECTROCHEMICAL SYNTHESIS OF CHLORO-CHITOSAN

CROSS REFERENCE TO RELATED APPLICATIONS

This application claims the benefit of, and priority to, International Patent Application No. PCT/US2013/024307 filed on Feb. 1, 2013, which, in turn, claims the benefit of, and priority to, U.S. Provisional Patent Application Ser. No. 61/594,619, filed Feb. 3, 2012, the entire disclosures of each of which are hereby incorporated by reference in their entirety.

BACKGROUND

The present disclosure provides processes for modifying chitosan and the resulting modified chitosan. Methods for using the resulting modified chitosan, are also provided.

Chitosan is a linear, high molecular weight, crystalline polysaccharide of $\beta$-(1→4) linked N-acetyl-D-glucosamine. It is produced by the alkaline N-deacetylation of chitin, the second most abundant natural polymer after cellulose.

Changing the acetamide group of chitin to amine in chitosan increases the reactivity of chitosan, making it a better chelation and adsorption agent than chitin. The adsorption capacity of chitosan has been further enhanced using physical modifications, including conditioning as gel beads and the formation of microcrystalline chitosan.

Chitosan is a biocompatible, biodegradable, and renewable material. Chitosan is also a film-forming, hydrating, antibacterial material with wound healing properties. Chitosan has applications in the biomedical, agricultural, water treatment, waste treatment, food and beverage, cosmetics and toiletries, and biopharmaceutical fields.

Improved materials for use in the above applications, as well as methods for producing such materials, remain desirable.

SUMMARY

The present disclosure provides methods for synthesizing novel chitosan derivatives. In embodiments the chitosan derivatives may be chloro-chitosan derivatives.

In embodiments, a process of the present disclosure includes contacting chitosan with a solvent to form a chitosan solution; adding to the chitosan solution an acid selected from the group consisting of hydrochloric acid, hypochloric acid, organic acids, and combinations thereof, to reduce the pH of the chitosan solution to a pH from about 1 to about 6; applying a positive potential of from about 1.5 volts to about 50 volts to the chitosan solution by the introduction of a cathode and anode into the chitosan solution; forming a chloro-chitosan derivative in the chitosan solution; and recovering the chloro-chitosan derivative from the chitosan solution.

In other embodiments, a process of the present disclosure includes contacting chitosan with a solvent selected from the group consisting of water, alcohols and combinations thereof, to form a chitosan solution; adding to the chitosan solution an acid selected from the group consisting of hydrochloric acid, hypochlorous acid, acetic acid, and combinations thereof, to reduce the pH of the chitosan solution to a pH from about 1 to about 6; applying a positive potential of from about 1.5 volts to about 50 volts to the chitosan solution by the introduction of a cathode and anode into the chitosan solution; forming a chloro-chitosan derivative in the chitosan solution; and recovering the chloro-chitosan derivative from the chitosan solution.

BRIEF DESCRIPTION OF THE FIGURES

Various embodiments of the present disclosure will be described herein with reference to the following figures, wherein.

DETAILED DESCRIPTION

Figure 1:
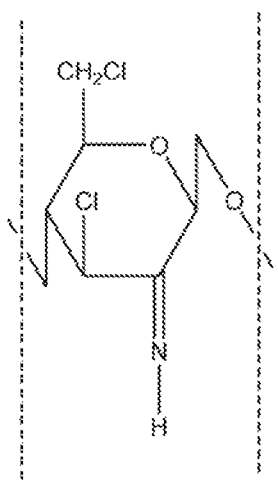
FIG. 1 is a depiction of the structure of a chloro-chitosan derivative of the present disclosure.

Disclosed herein is an electrochemical method for the synthesis of novel chitosan derivatives, including chloro-chitosan derivatives. These new derivatives of chitosan alter various properties of chitosan, including its affinity towards cations, by changing the functional groups on the chitosan polymer. The process results in formation of chloro groups on chitosan.

Chitosan possesses a primary amine, a primary hydroxyl and secondary hydroxyl groups. These reactive functional groups make chitosan amenable to further functionalization and modification.

In accordance with the present disclosure, an electrochemical process for modification of chitosan is utilized to prepare a chloro-chitosan biopolymer. The electrochemical process transforms chitosan by replacing chitosan's primary and secondary hydroxyl groups with chlorine.

To carry out the processes of the present disclosure, chitosan is dissolved in water or another suitable solvent such as alcohols. The volume of water or other suitable solvent used to form this solution may be from about 10 ml to about 10 liters, in embodiments from about 100 ml to about 1 liter. The amount of chitosan may vary, and can be present in amounts from about 0.1% to about 50% by weight of the solution, in embodiments from about 1% to about 10% by weight of the solution. The solution may be formed by addition of mineral or organic acid from 0.5% to 10% by weight, in embodiments from about 1% to 5% acid by weight. In embodiments, the solution may be formed with heating from about 10° C. to about 90° C., in embodiments from about 25° C. to about 70° C. The solution may also be formed with mixing at a rate of from about 1 revolutions per minute (rpm) to about 1000 rpm, in embodiments from about 5 rpm to about 100 rpm. The solution may be formed over a period of time from about 10 minutes to about 48 hours, in embodiments from about 1 hour to about 10 hours. The resulting chitosan solution may have a pH from about 1 to about 9, in embodiments from about 2 to about 8.

Once formed, the pH of the solution may then be lowered by addition of an acid thereto. Suitable acids include, for example, hydrochloric acid (HCl), hypochlorous acid or organic acids like acetic acid, combinations thereof, and the like. The amount of acid added to the solution will depend on the amount of chitosan and solvent utilized to form the solution. The acid may have a molarity from about 0.1 to about 10, in embodiments from about 0.5 to about 2. In embodiments, the acid may be added to lower the pH of the chitosan solution so that the chitosan solution possesses a pH from less than 1 to about 6.5, in embodiments from about 2 to about 6.

After the pH of the solution has been lowered, a positive potential is applied to the chitosan solution to form a chloro-chitosan derivative.

In embodiments, a positive potential equal to or greater than 1.5 volts (V) versus Open Circuit Potential (OCP) is applied to the solution, by the introduction of a cathode and amode into the solution. Cathodes may be made of any suitable material within the purview of one skilled in the art, including stainless steel, graphite, gold, silver or platinum. The positive potential may be, in embodiments, from about 1.5 volts to about 50 volts, in embodiments from about 1.75 volts to about 15 volts.

Application of a high positive potential to the chitosan solution that has been treated with HCl or similar acid oxidizes chloride ions and generates chlorine. The generated chlorine is highly reactive and reacts with the chitosan in the chitosan solution to produce a chloro-chitosan derivative with chlorine in place of the hydroxyl functional groups and may be accompanied by formation of a double bond between carbon and nitrogen.

The chloro-chitosan derivative thus produced by the processes of the present disclosure includes monomers having the general structure set forth in FIG. 1.

The chloro-chitosan may be recovered by methods within the purview of one skilled in the art, including filtering, skimming from top of the solution, and drying the solution containing the chloro-chitosan.

The electrochemical synthetic processes of the present disclosure are scalable and provide facile process control parameters. Limited use of toxic oxidizing and reducing agents in the processes of the present disclosure provides an environmentally friendly process. Further, use of the electrochemical synthetic process enables deposition of the chloro-chitosan derivatives as a thin film or a patterned structure.

Once formed, the resulting chitosan derivatives, may be used as chelating agents. Chloro-chitosan retains its natural biocompatibility and retains chitosan's hydrating properties. Substitution of hydroxyl by chlorine enhances metal chelation and binding properties of chitosan, and thus the chloro-chitosan derivative performs better than natural chitosan in pharmaceutical applications, including controlled release drug delivery devices, fat reduction, protective coatings over fruits and vegetables, and hemostatic bandages.

For example, the chloro-chitosan derivative may be contacted with another component to form a hydrogel suitable for use as a coating for food or as a hemostat. Suitable components for forming a hydrogel include, for example, additives such as surfactants and solubilizing agents. In some embodiments, suitable solubilizers include polyethoxylated fatty acid esters of sorbitan, sometimes referred to herein as Polysorbates, including those sold under the name TWEEN™. Examples of such Polysorbates include Polysorbate 80 (TWEEN™ 80), Polysorbate 20 (TWEEN™ 20), Polysorbate 60 (TWEEN™ 60), Polysorbate 65 (TWEEN™ 65), Polysorbate 85 (TWEEN™ 85), and the like, and combinations including these materials with other similar surfactants.

Biodegradability of chitosan has also been exploited in the fertilizer industry. Chloro-chitosan has a higher electronegativity and thus provides a higher loading of fertilizer per unit mass of polymer than natural chitosan. Thus, the chloro-chitosan derivatives may be combined with other fertilizers to enhance efficiency and loading of fertilizer with controlled release.

The presence of chlorine also enhances the antimicrobial properties of chitosan, so the chloro-chitosan derivatives of the present disclosure have wide applications in the biomedical field, including as antiseptics and/or disinfectants.

The following Examples are provided to illustrate, but not limit, the features of the present disclosure so that those skilled in the art may be better able to practice the features of the disclosure described herein.

EXAMPLE 1

Electrodeposition of chitosan. A chitosan solution was made by adding about 1.5 grams of a low molecular weight chitosan (obtained from Sigma Aldrich (75-85% deacetylated)) to about 120 ml deionized (DI) water under constant stirring at a rate of about 100 rpm. Hydrochloric acid (HCl), having a molarity (M) of about 1 M, was then added drop wise until all the chitosan was dissolved, which occurred as the solution reached a pH of about 2.

A polished type 304 stainless steel (metal composition approximately 19% Cr 9% Ni, with the balance Fe) was chosen as the working electrode. A platinum wire served as the counter electrode. A Gamry Reference 600 potentiostat was used to perform electrochemistry and Gamry Instrument Framework software was used for control and monitoring of voltage and current.

To form a chloro-chitosan derivative, a controlled potential coulometry at a voltage of about 1.5 V (versus Ag/AgCl reference electrode) was applied for about 10 minutes. The chloro-chitosan derivative thus produced was in the form of froth and recovered by skimming from top of the solution. The resulting derivative was then dried and crushed mechanically to form a powder for spectroscopic analysis and absorption experiments.

EXAMPLE 2

Raman Spectroscopy was then performed on the powdered polymer produced in Example 1. A Nicolet Almega dispersive Raman spectrometer, with a 785 nm laser source, was used for analysis. (OMNIC for Nicolet Almega, software version 7.3, was used to process data.) Powdered samples were placed on quartz slides and Raman microspectroscopy in reflectance mode was used for data acquisition. Data were collected in the 3600-400 $cm^{-1}$ range. An average of 10 scans with 5 second accumulation time for each exposure was collected. For comparison, a chitosan solution at pH 3 was dried (without any applied potential) on stainless steel and similarly analyzed.

Figure 2:
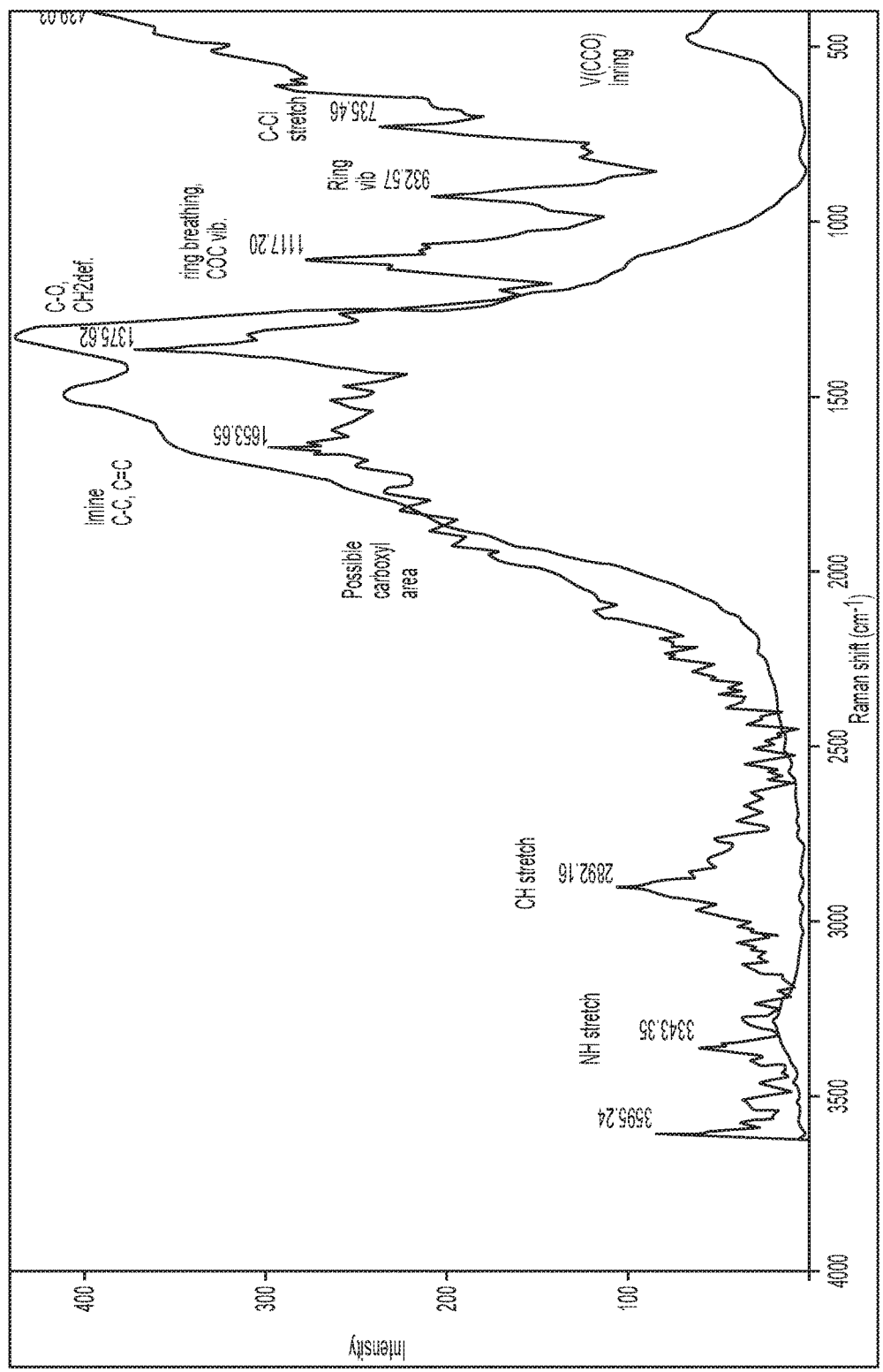
FIG. 2 is a Raman spectra of a chloro-chitosan derivative of the present disclosure.

FIG. 2 illustrates the resulting Raman spectrum, which showed an imine peak at 1653 $cm^{-1}$, a C—Cl stretching peak at 735 $cm^{-1}$, and a N—H stretching peak at 3343 $cm^{-1}$. Based on these findings, the structure of the chloro-chitosan was confirmed, as shown in FIG. 2. The higher electronegativity of chlorine (3.1 kJ/mol) than hydroxyl ion (2.8 kJ/mol), resulted in an increased cationic affinity of the chloro-chitosan compared to naturally occurring chitosan. Further, the presence of chlorine enhanced the antibacterial properties of chitosan, making the chloro-chitosan derivative a better antibacterial agent.

While the above description contains many specific details of methods in accordance with this disclosure, these specific details should not be construed as limitations on the scope of the disclosure, but merely as exemplifications of preferred embodiments thereof. Those skilled in the art will envision many other possible variations that are all within the scope and spirit of the disclosure.

What is claimed is:

1. A process comprising:
contacting chitosan with a solvent selected from the group consisting of water, alcohols and combinations thereof, with heating to a temperature from about 25° C. to about 70° C. to form a chitosan solution having chitosan present in an amount from about 1% to about 10% by weight of the solution;
adding to the chitosan solution an acid selected from the group consisting of hydrochloric acid, hypochlorous acid, and combinations thereof, to reduce the pH of the chitosan solution to a pH from about 1 to about 6;
applying a positive potential of from about 1.5 volts to about 50 volts to the chitosan solution by the introduction of a cathode and anode into the chitosan solution;
forming a chloro-chitosan as a froth in the chitosan solution; and
recovering the chloro-chitosan from the froth of the chitosan solution, wherein the chloro-chitosan includes a monomer of the following formula:

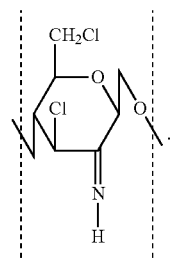

2. The process of claim 1, wherein the chitosan solution is formed with mixing at a rate of from about 1 revolution per minute to about 1000 revolutions per minute.

3. The process of claim 1, wherein the chitosan solution is formed over a period of time from about 1 minute to about 48 hours.

4. The process of claim 1, further comprising contacting a drug with the chloro-chitosan to form a drug delivery device.

5. The process of claim 1, further comprising contacting a polyethoxylated fatty acid ester of sorbitan with the chloro-chitosan to form a hydrogel.

* * * * *